United States Patent
Abdul-Hafiz

(10) Patent No.: US 9,924,897 B1
(45) Date of Patent: Mar. 27, 2018

(54) HEATED REPROCESSING OF PHYSIOLOGICAL SENSORS

(71) Applicant: MASIMO CORPORATION, Irvine, CA (US)

(72) Inventor: Yassir Kamel Abdul-Hafiz, Irvine, CA (US)

(73) Assignee: MASIMO CORPORATION, Irvine, CA (US)

( * ) Notice: Subject to any disclaimer, the term of this patent is extended or adjusted under 35 U.S.C. 154(b) by 225 days.

(21) Appl. No.: 14/733,808

(22) Filed: Jun. 8, 2015

Related U.S. Application Data

(60) Provisional application No. 62/011,256, filed on Jun. 12, 2014.

(51) Int. Cl.
| | |
|---|---|
| *A61B 5/00* | (2006.01) |
| *A61B 5/1455* | (2006.01) |
| *A61B 5/1495* | (2006.01) |

(52) U.S. Cl.
CPC ........ *A61B 5/14552* (2013.01); *A61B 5/1495* (2013.01); *A61B 2560/00* (2013.01)

(58) Field of Classification Search
CPC ......... Y10T 29/49815; Y10T 29/49817; Y10T 29/49821; Y10T 29/49721; Y10T 29/4973; Y10T 29/49764; Y10T 29/49771; B29C 73/34; A61B 5/021; A61B 5/02108; A61B 5/02166; A61B 5/02125
USPC .......................................... 156/703, 704, 711
See application file for complete search history.

(56) References Cited

U.S. PATENT DOCUMENTS

| | | | |
|---|---|---|---|
| 4,466,852 A | * | 8/1984 | Beltz ..................... B24B 37/345 134/59 |
| 4,960,128 A | | 10/1990 | Gordon et al. |
| 4,964,408 A | | 10/1990 | Hink et al. |
| 5,041,187 A | | 8/1991 | Hink et al. |
| 5,069,213 A | | 12/1991 | Polczynski |
| 5,163,438 A | | 11/1992 | Gordon et al. |
| 5,319,355 A | | 6/1994 | Russek |
| 5,337,744 A | | 8/1994 | Branigan |
| 5,341,805 A | | 8/1994 | Stavridi et al. |
| D353,195 S | | 12/1994 | Savage et al. |
| D353,196 S | | 12/1994 | Savage et al. |
| 5,377,676 A | | 1/1995 | Vari et al. |
| D359,546 S | | 6/1995 | Savage et al. |
| 5,431,170 A | | 7/1995 | Mathews |

(Continued)

OTHER PUBLICATIONS

US 8,845,543, 09/2014, Diab et al. (withdrawn)

*Primary Examiner* — Jason L Vaughan
(74) *Attorney, Agent, or Firm* — Knobbe Martens Olson & Bear LLP

(57) ABSTRACT

Methods of reprocessing physiological sensors may include applying heat to a physiological sensor so as to efficiently remove adhesives, adhesive layers, and/or other disposable components of the sensor. Heat may be applied to the physiological sensor efficiently via a medium, such as an aqueous solution (for example, water). Reusable components of the physiological sensor may then be reassembled with new disposable components and/or adhesives to produce a reprocessed sensor. The methods may further include testing and/or replacement of various reusable sensor components, testing of the reprocessed sensor, cleaning of the reprocessed sensor and/or sensor components, and/or sterilization of the reprocessed sensor, among other steps.

16 Claims, 12 Drawing Sheets

(56) References Cited

U.S. PATENT DOCUMENTS

| | | | |
|---|---|---|---|
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,842 A * | 6/1998 | Tanaka .................. B29C 63/0013 156/701 |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,594,890 B2 * | 7/2003 | Arai ..................... B24B 7/228 29/426.1 |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,821,376 B1 * | 11/2004 | Rayssac ............ H01L 21/67092 156/382 |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |

(56) References Cited

U.S. PATENT DOCUMENTS

| | | |
|---|---|---|
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,730,600 B2 * | 6/2010 | Nishida .............. B08B 3/04 156/247 |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,909,959 B2 * | 3/2011 | Tada .................. C09J 5/00 156/706 |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |

(56) References Cited

U.S. PATENT DOCUMENTS

| | | | |
|---|---|---|---|
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,302,651 B2 * | 11/2012 | Nakada | B32B 43/006 |
| | | | 156/703 |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,443,864 B2 * | 5/2013 | Thallner | H01L 21/67092 |
| | | | 156/703 |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,584,345 B2 | 10/2013 | Al-Ali et al. |
| 8,577,431 B2 | 11/2013 | Lamego et al. |
| 8,581,732 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |

(56) References Cited

U.S. PATENT DOCUMENTS

| | | | |
|---|---|---|---|
| 8,998,809 B2 | 4/2015 | Kiani | |
| 2006/0080819 A1* | 4/2006 | McAllister | G06K 17/00 29/403.3 |
| 2009/0247924 A1 | 10/2009 | Lamego et al. | |
| 2009/0275844 A1 | 11/2009 | Al-Ali | |
| 2009/0299157 A1 | 12/2009 | Telfort et al. | |
| 2010/0004518 A1 | 1/2010 | Vo et al. | |
| 2010/0030040 A1 | 2/2010 | Poeze et al. | |
| 2010/0261979 A1 | 10/2010 | Kiani | |
| 2011/0001605 A1 | 1/2011 | Kiani et al. | |
| 2011/0082711 A1 | 4/2011 | Poeze et al. | |
| 2011/0105854 A1 | 5/2011 | Kiani et al. | |
| 2011/0208015 A1 | 8/2011 | Welch et al. | |
| 2011/0209915 A1 | 9/2011 | Telfort et al. | |
| 2011/0213212 A1 | 9/2011 | Al-Ali | |
| 2011/0230733 A1 | 9/2011 | Al-Ali | |
| 2011/0237911 A1 | 9/2011 | Lamego et al. | |
| 2012/0059267 A1 | 3/2012 | Lamego et al. | |
| 2012/0116175 A1 | 5/2012 | Al-Ali et al. | |
| 2012/0118510 A1* | 5/2012 | Banda | B32B 38/10 156/704 |
| 2012/0179006 A1 | 7/2012 | Jansen et al. | |
| 2012/0209082 A1 | 8/2012 | Al-Ali | |
| 2012/0209084 A1 | 8/2012 | Olsen et al. | |
| 2012/0227739 A1 | 9/2012 | Kiani | |
| 2012/0258315 A1* | 10/2012 | Foulc | C08J 5/08 428/416 |
| 2012/0265039 A1 | 10/2012 | Kiani | |
| 2012/0283524 A1 | 11/2012 | Kiani et al. | |
| 2012/0286955 A1 | 11/2012 | Welch et al. | |
| 2012/0296178 A1 | 11/2012 | Lamego et al. | |
| 2012/0319816 A1 | 12/2012 | Al-Ali | |
| 2012/0330112 A1 | 12/2012 | Lamego et al. | |
| 2013/0023775 A1 | 1/2013 | Lamego et al. | |
| 2013/0045685 A1 | 2/2013 | Kiani | |
| 2013/0046204 A1 | 2/2013 | Lamego et al. | |
| 2013/0041591 A1 | 3/2013 | Lamego | |
| 2013/0060108 A1 | 3/2013 | Schurman et al. | |
| 2013/0060147 A1 | 3/2013 | Welch et al. | |
| 2013/0079618 A1* | 3/2013 | Sandmore | A61B 5/0478 600/393 |
| 2013/0096405 A1 | 4/2013 | Garfio | |
| 2013/0096936 A1 | 4/2013 | Sampath et al. | |
| 2013/0109935 A1 | 5/2013 | Al-Ali et al. | |
| 2013/0162433 A1 | 6/2013 | Muhsin et al. | |
| 2013/0188323 A1* | 7/2013 | Hunt | H05K 3/321 361/750 |
| 2013/0190581 A1 | 7/2013 | Al-Ali et al. | |
| 2013/0197328 A1 | 8/2013 | Diab et al. | |
| 2013/0211214 A1 | 8/2013 | Olsen | |
| 2013/0243021 A1 | 9/2013 | Siskavich | |
| 2013/0253334 A1 | 9/2013 | Al-Ali et al. | |
| 2013/0274571 A1 | 10/2013 | Diab et al. | |
| 2013/0296672 A1 | 11/2013 | O'Neil et al. | |
| 2013/0317370 A1 | 11/2013 | Dalvi et al. | |
| 2013/0324808 A1 | 12/2013 | Al-Ali et al. | |
| 2013/0331670 A1 | 12/2013 | Kiani | |
| 2013/0338461 A1 | 12/2013 | Lamego et al. | |
| 2014/0012100 A1 | 1/2014 | Al-Ali et al. | |
| 2014/0025306 A1 | 1/2014 | Weber et al. | |
| 2014/0034353 A1 | 2/2014 | Al-Ali et al. | |
| 2014/0051952 A1 | 2/2014 | Reichgott et al. | |
| 2014/0051953 A1 | 2/2014 | Lamego et al. | |
| 2014/0051954 A1 | 2/2014 | Al-Ali et al. | |
| 2014/0058230 A1 | 2/2014 | Abdul-Hafiz et al. | |
| 2014/0066783 A1 | 3/2014 | Kiani et al. | |
| 2014/0077956 A1 | 3/2014 | Sampath et al. | |
| 2014/0081100 A1 | 3/2014 | Muhsin et al. | |
| 2014/0081175 A1 | 3/2014 | Telfort | |
| 2014/0094667 A1 | 4/2014 | Schurman et al. | |
| 2014/0100434 A1 | 4/2014 | Diab et al. | |
| 2014/0114199 A1 | 4/2014 | Lamego et al. | |
| 2014/0120564 A1 | 5/2014 | Workman et al. | |
| 2014/0121482 A1 | 5/2014 | Merritt et al. | |
| 2014/0121483 A1 | 5/2014 | Kiani | |
| 2014/0125495 A1 | 5/2014 | Al-Ali | |
| 2014/0127137 A1 | 5/2014 | Bellott et al. | |
| 2014/0128696 A1 | 5/2014 | Al-Ali | |
| 2014/0128699 A1 | 5/2014 | Al-Ali et al. | |
| 2014/0129702 A1 | 5/2014 | Lamego et al. | |
| 2014/0135588 A1 | 5/2014 | Al-Ali et al. | |
| 2014/0142401 A1 | 5/2014 | Al-Ali et al. | |
| 2014/0142402 A1 | 5/2014 | Al-Ali et al. | |
| 2014/0163344 A1 | 6/2014 | Al-Ali | |
| 2014/0163402 A1 | 6/2014 | Lamego et al. | |
| 2014/0166076 A1 | 6/2014 | Kiani et al. | |
| 2014/0171763 A1 | 6/2014 | Diab | |
| 2014/0180038 A1 | 6/2014 | Kiani | |
| 2014/0180154 A1 | 6/2014 | Sierra et al. | |
| 2014/0194709 A1 | 7/2014 | Al-Ali et al. | |
| 2014/0194711 A1 | 7/2014 | Al-Ali | |
| 2014/0194766 A1 | 7/2014 | Al-Ali et al. | |
| 2014/0200420 A1 | 7/2014 | Al-Ali | |
| 2014/0200422 A1 | 7/2014 | Weber et al. | |
| 2014/0206963 A1 | 7/2014 | Al-Ali | |
| 2014/0213864 A1 | 7/2014 | Abdul-Hafiz et al. | |
| 2014/0243627 A1 | 8/2014 | Diab et al. | |
| 2014/0266790 A1 | 9/2014 | Al-Ali et al. | |
| 2014/0275808 A1 | 9/2014 | Poeze et al. | |
| 2014/0275835 A1 | 9/2014 | Lamego et al. | |
| 2014/0275871 A1 | 9/2014 | Lamego et al. | |
| 2014/0275872 A1 | 9/2014 | Merritt et al. | |
| 2014/0275881 A1 | 9/2014 | Lamego et al. | |
| 2014/0288400 A1 | 9/2014 | Diab et al. | |
| 2014/0296664 A1 | 10/2014 | Bruinsma et al. | |
| 2014/0303520 A1 | 10/2014 | Telfort et al. | |
| 2014/0309506 A1 | 10/2014 | Lamego et al. | |
| 2014/0309559 A1 | 10/2014 | Telfort et al. | |
| 2014/0316228 A1 | 10/2014 | Blank et al. | |
| 2014/0323825 A1 | 10/2014 | Al-Ali et al. | |
| 2014/0330092 A1 | 11/2014 | Al-Ali et al. | |
| 2014/0330098 A1 | 11/2014 | Merritt et al. | |
| 2014/0330099 A1 | 11/2014 | Al-Ali et al. | |
| 2014/0333440 A1 | 11/2014 | Kiani | |
| 2014/0336481 A1 | 11/2014 | Shakespeare et al. | |
| 2014/0343436 A1 | 11/2014 | Kiani | |
| 2015/0018650 A1 | 1/2015 | Al-Ali et al. | |

\* cited by examiner

HEATED REPROCESSING OF PHYSIOLOGICAL SENSORS

PRIORITY CLAIM AND RELATED APPLICATIONS

This application claims a priority benefit under 35 U.S.C. § 119 to U.S. Provisional Patent Application No. 62/011,256, filed Jun. 12, 2014, and titled "HEATED REPROCESSING OF PHYSIOLOGICAL SENSORS." The entire disclosure of each of the above items is hereby made part of this specification as if set forth fully herein and incorporated by reference for all purposes, for all that it contains.

BACKGROUND

The present disclosure relates generally to physiological sensors and specifically to reprocessing or refurbishing of physiological sensors.

Patient monitoring of various physiological parameters of a patient is important to a wide range of medical applications. Oximetry is one of the techniques that has developed to accomplish the monitoring of some of these physiological characteristics. It was developed to study and to measure, among other things, the oxygen status of blood. Pulse oximetry—a noninvasive, widely accepted form of oximetry—relies on a physiological sensor attached externally to a patient to output signals indicative of various physiological parameters, such as a patient's constituents and/or analytes, including for example a percent value for arterial oxygen saturation, carbon monoxide saturation, methemoglobin saturation, fractional saturations, total hematocrit, billirubins, perfusion quality, or the like. A pulse oximetry system generally includes a patient monitor, a communications medium such as a cable, and/or a physiological sensor having light emitters and a detector, such as one or more LEDs and a photodetector. The sensor is attached to a tissue site, such as a finger, toe, ear lobe, nose, hand, foot, or other site having pulsatile blood flow which can be penetrated by light from the emitters. The detector is responsive to the emitted light after attenuation by pulsatile blood flowing in the tissue site. The detector outputs a detector signal to the monitor over the communication medium, which processes the signal to provide a numerical readout of physiological parameters such as oxygen saturation ($SpO_2$) and/or pulse rate.

High fidelity pulse oximeters capable of reading through motion induced noise are disclosed in U.S. Pat. Nos. 7,096,054, 6,813,511, 6,792,300, 6,770,028, 6,658,276, 6,157,850, 6,002,952 5,769,785, and 5,758,644, which are assigned to Masimo Corporation of Irvine, Calif. ("Masimo Corp.") and are incorporated by reference herein. Advanced physiological monitoring systems can incorporate pulse oximetry in addition to advanced features for the calculation and display of other blood parameters, such as carboxyhemoglobin (HbCO), methemoglobin (HbMet), total hemoglobin (Hbt), total Hematocrit (Hct), oxygen concentrations, glucose concentrations, blood pressure, electrocardiogram data, temperature, and/or respiratory rate as a few examples. Typically, the physiological monitoring system provides a numerical readout of and/or waveform of the measured parameter. Advanced physiological monitors and multiple wavelength optical sensors capable of measuring parameters in addition to $SpO_2$, such as HbCO, HbMet and/or Hbt are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, assigned to Masimo Laboratories, Inc. and incorporated by reference herein. Further, noninvasive blood parameter monitors and optical sensors including Rainbow™ adhesive and reusable sensors and RAD-57™ and Radical-7™ monitors capable of measuring $SpO_2$, pulse rate, perfusion index (PI), signal quality (SiQ), pulse variability index (PVI), HbCO and/or HbMet, among other parameters, are also commercially available from Masimo Corp.

SUMMARY

For purposes of summarizing the disclosure, certain aspects, advantages and novel features of several embodiments have been described herein. It is to be understood that not necessarily all such advantages can be achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as can be taught or suggested herein.

Methods and processes of reprocessing physiological sensors may include applying heat to a physiological sensor so as to efficiently remove adhesives, adhesive layers, and/or other disposable components of the sensor. Heat may be applied to the physiological sensor efficiently via a medium, such as an aqueous solution (for example, water). Heat can also be applied through the use of heat guns, heat lamps, an oven, a hot bed or any other heat application devices as would be understood to those of skill in the art from the present disclosure. Once the tape layers are sufficiently heated, the components can be removed without damage. Reusable components of the physiological sensor may then be reassembled with new disposable components and/or adhesives to produce a reprocessed sensor. The methods may further include testing and/or replacement of various reusable sensor components, testing of the reprocessed sensor, and/or sterilization of the reprocessed sensor.

BRIEF DESCRIPTION OF THE DRAWINGS

Throughout the drawings, reference numbers are re-used to indicate correspondence between referenced elements. The drawings are provided to illustrate embodiments of the inventions described herein and not to limit the scope thereof.

DETAILED DESCRIPTION

Introduction

Figure 1A:
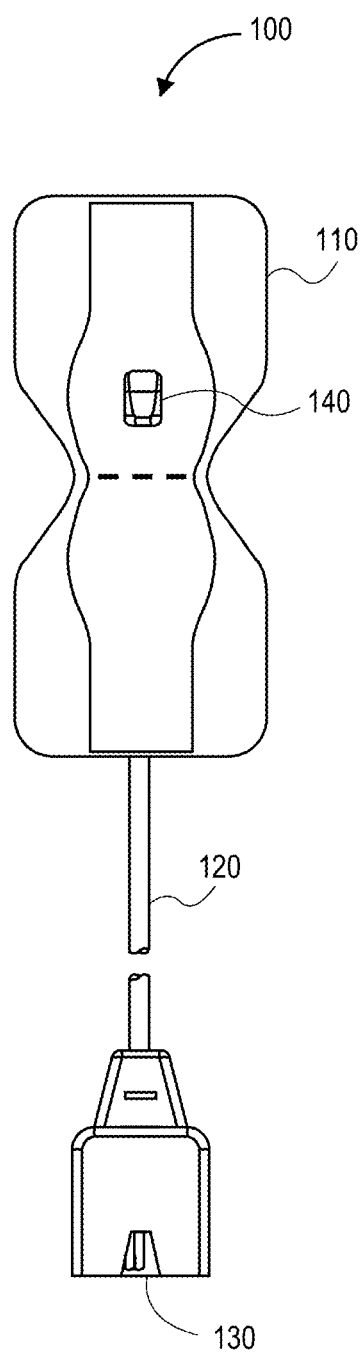
FIGS. 1A-1C illustrate an example non-invasive physiological sensor which can be used with a sensor reprocessing method, according to embodiments of the disclosure.

In order to reduce costs, some hospitals or medical institutions choose to purchase refurbished or reprocessed sensors. Typically, these sensors are single-use sensors and are meant to be used by a single patient. After these sensors are used, they may be reprocessed such that portions of the sensors may be reused. Reprocessing of sensors may include receiving used sensors, usually from the hospitals, and replacing disposable (for example, adhesive) portions of the sensors. Reprocessing includes operations performed to render a used reusable or single-use device patient-ready or to allow an unused product that has been opened to be made patient-ready. Reprocessing can be done in-house or by a third-party reprocessor. Whether reprocessesing is done in-house or through a third party, reprocessing may include cleaning, sterilization, function testing, and/or replacement of sensor components, among other steps.

Reprocessing of a sensor typically includes disassembly of a used sensor into various disposable and reusable sensor components. Disposable sensor components may be replaced, while reusable sensor components may be reused. The replaced disposable components and the reusable components may be reassembled into a reprocessed sensor and, as mentioned above, the reprocessed sensor may be cleaned, sterilized, and/or tested to ensure expected performance of the sensor.

Physiological sensors often include one or more adhesive layers (for example, tape layers), and/or various components that are assembled using adhesives. Disassembly of the sensor may involve removing such adhesives and/or adhesive layers without damaging other reusable sensor components. Disclosed herein are methods of efficient disassembly of physiological sensors, including removal of adhesives and/or adhesive layers, using heat, such as heat applied from a heat source and/or via a medium such as a fluid (for example, water, oil, and/or the like), solid, or semi-solid. Such methods may enable disassembly of the sensors without damage to reusable sensor components. Further, such methods may enable removal of adhesives from reusable sensor components, and cleaning of those reusable sensor components.

Re-use of reusable sensor components can decrease reliability of sensor readings, and/or degraded sensor performance, as the sensor components may suffer from wear, damage, misalignment, and/or the like due to use. On the other hand, if reprocessing institutes strict functional testing procedures, sensors can be disposed of even if a large portion of a sensor, other than a specific sensing component (such as an emitter or detector), is still within specification. Accordingly, the methods disclosed herein may additionally include testing of individual reusable sensor components and/or an entire reprocessed sensor.

Because reprocessing or refurbishing of a physiological sensor, as described herein, reuses large portions of an existing sensor, the material costs for reprocessing a sensor may be significantly lower than the material costs for making an entirely new sensor. Further, costs of reprocessed sensors may be further reduced by the methods described herein as disassembly, including removal of adhesives and/or adhesive layers, may be accomplished rapidly and efficiently by applying fluids to the used sensors.

As mentioned above, methods of reprocessing physiological sensors disclosed herein may include applying heat to a physiological sensor so as to efficiently remove adhesives, adhesive layers, and/or other disposable components of the sensor. Heat may be applied to the physiological sensor efficiently via a medium, such as an aqueous solution (for example, water). Reusable components of the physiological sensor may then be reassembled with new disposable components and/or adhesives to produce a reprocessed sensor. The methods may further include testing and/or replacement of various reusable sensor components, testing of the reprocessed sensor, cleaning of the reprocessed sensor and/or sensor components, and/or sterilization of the reprocessed sensor, among other steps.

As used herein, the term "cleaning" is a broad term encompassing its plain and ordinary meaning and includes, without limitation, removal of visible contaminants and environmental debris (including microscopic particles of tissue, body waste, body fluids, dirt, and/or dust). As used herein, the term "function testing" (also referred to as simply "testing") is a broad term encompassing its plain and ordinary meaning and includes, without limitation, verifying that a device performs, or will perform, as intended. As used herein, the term "sterilization" is a broad term encompassing its plain and ordinary meaning and includes, without limitation, the process of meeting domestic and/or international sterilization standards, such as meeting a sterility assurance level of $10^{-6}$ (i.e. a theoretical one in a million chance that an organism could survive).

As used herein, the term "reusable," as used in reference to various sensors and/or sensor components, is a broad term encompassing its plain and ordinary meaning and includes, without limitation, sensor and/or sensor components that are generally still useful and/or easily reprocessed or refurbished after a single use. For example, electronic sensor components are generally not destroyed and may generally be reused (assuming the sensor components still function according to specification, as described below) after a single use with a patient. In some embodiments, however, it is understood that such "reusable" sensor components may be damaged after a single use and may therefore be disposed of. In contrast, as used herein, the term "disposable," as used in reference to various sensors and/or sensor components, is a broad term encompassing its plain and ordinary meaning and includes, without limitation, sensor and/or sensor components that are generally not still useful after a single use and are therefore usually disposed of. For example, adhesive layers of a sensor are generally destroyed and/or contaminated after a single use, making refurbishment or reprocessing difficult or uneconomical. In some embodiments, however, it is understood that such "disposable" sensor components may be reprocessed and reused.

Example Physiological Sensors

Various example non-invasive physiological sensors that may be used with the sensor reprocessing methods described herein are described below in reference to FIGS. 1A-1C, 2A-2D, 3, 4A-4B, and 5A-5B. For the sake of brevity and clarity, the description of each of these figures below focuses on unique aspects of each example sensor. However, the various features and aspects described in reference to any one example sensor may apply equally to other example sensors. Accordingly, the described sensors provide many examples of different combinations of sensor components that may be used in the sensor reprocessing methods described below.

Figure 1B:
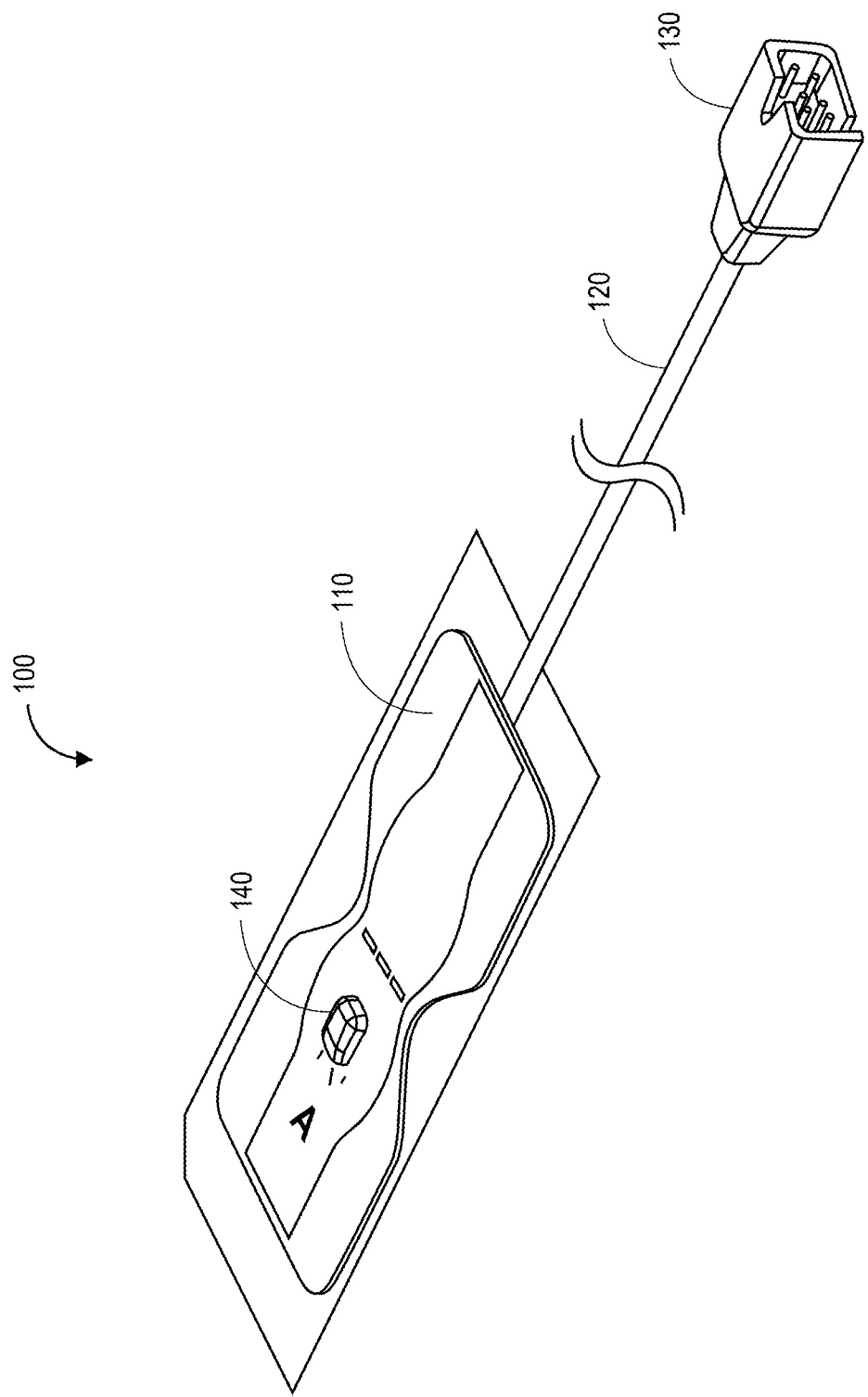
Figure 1C:
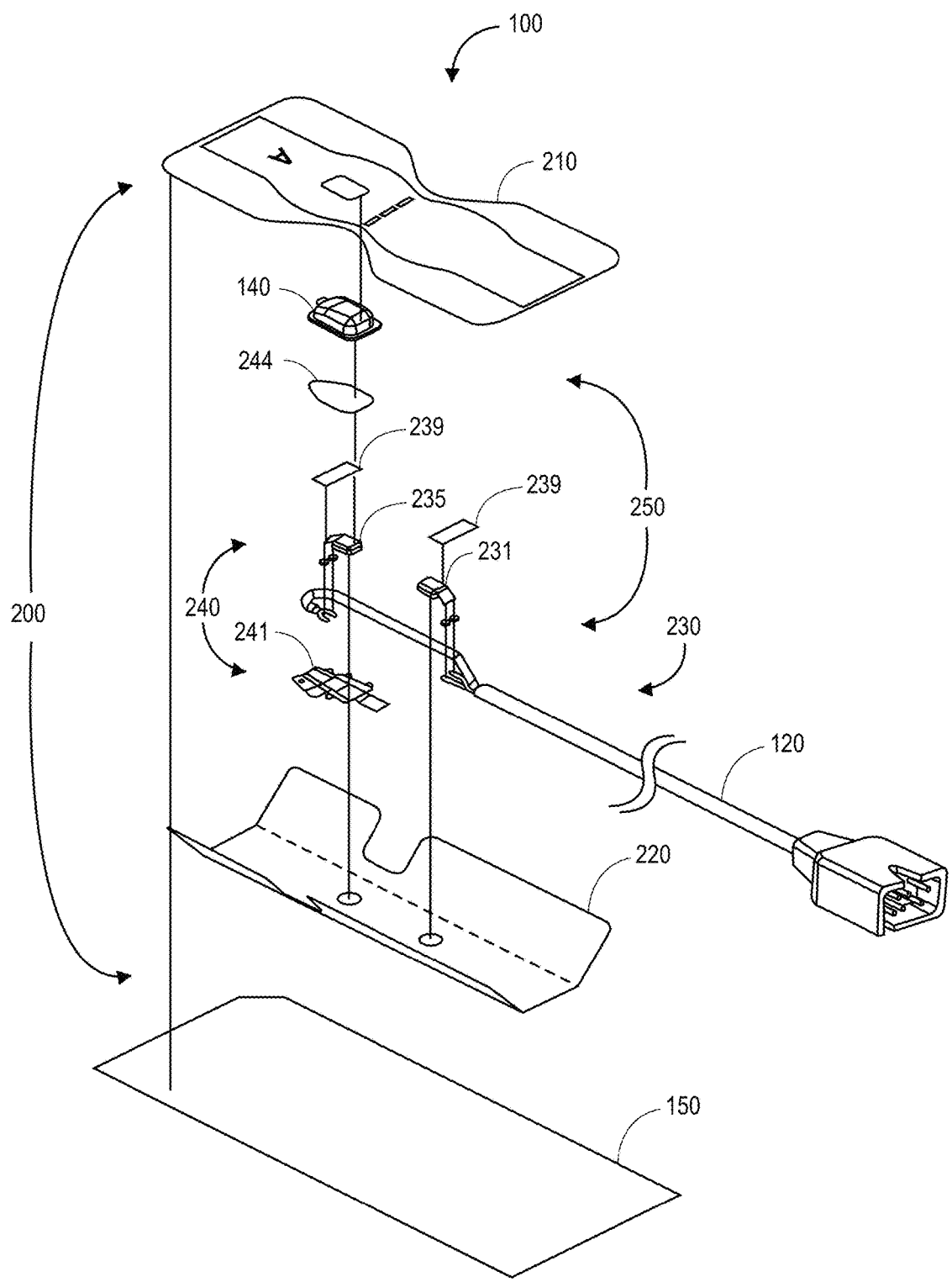

FIGS. 1A-1C illustrate an example non-invasive physiological sensor 100 which can be used with the sensor reprocessing methods described herein, according to various embodiments. The sensor 100 may allow for the measurement of blood constituents and related parameters, including oxygen saturation, HbCO, HBMet and/or pulse rate. The sensor 100 may advantageously be a non-invasive optical sensor capable of emitting light and outputting one or more signals indicative of attenuation of that light by body tissue. For example, the sensor 100 may be a pulse oximeter sensor including, for example, a red emitter, an infrared emitter, and a photodiode detector. The sensor 100 may be attached to a patient's finger, earlobe, or foot. For a finger, the sensor can be configured so that the emitters project light from one side of the finger, through the outer tissue of the finger, and into the blood vessels and capillaries contained inside. The photodiode can be positioned at the opposite side of the finger to detect the emitted light as it emerges from the outer tissues of the finger. The photodiode can generate a signal based on the emitted light and relay that signal to the sensor 100. The sensor 100 can determine blood oxygen saturation by, for example, computing the differential absorption by the arterial blood of the two or more wavelengths emitted by the sensor. In certain embodiments, the sensor 100 utilizes an adhesive attachment mechanism, such as an adhesive layer, for attaching the sensor 100 to a tissue site. In some embodiments, the sensor can be disposable, reusable, or partially reusable and partially disposable.

As shown in FIGS. 1A-1C the sensor 100 includes a body 110, a cable 120, and a connector 130. The body 110 is configured to wrap around a fingertip and attach adhesively to the fingertip, and incorporates an emitter 231 (FIG. 1C) and a detector 235 (FIG. 1C) that provide physiological measurements responsive to a patient's blood oxygen saturation, as described above. The body 110 also incorporates a flexible housing 140 configured to enclose a shielded detector assembly 240 (FIG. 1C). Advantageously, the flexible housing 140 optically shields the detector 235 (FIG. 1C), blocking ambient and piped light. The cable 120 provides electrical communication between the emitter 231 (FIG. 1C) and detector 235 (FIG. 1C) and the connector 130. The connector 130 is adapted to a patient cable, which electrically and mechanically connects the sensor 100 to a monitor (not shown).

As shown in FIG. 1C, the sensor 100 includes a cable assembly 230, a shielded detector assembly 240, a housing assembly 250, a tape assembly 200, and a flexible housing 140. The cable assembly includes the cable 120, the emitter 231, the shielded detector assembly 240, and insulating tape 239. The shielded detector assembly 240 includes the detector 235, an electromagnetic interference (EMI) shield 241, and a light barrier 244. The housing assembly 250 includes the cable assembly 230 and the flexible housing 140. The tape assembly 200 includes a face tape 210, a trifold wrap 220, and a release liner 150, as described in detail with respect to FIGS. 2A-2D. Various aspects of the sensor 100 are described in further detail in U.S. Pat. No. 7,280,858, titled "Pulse Oximetry Sensor," which is hereby incorporated by reference herein in its entirety.

Figure 2A:
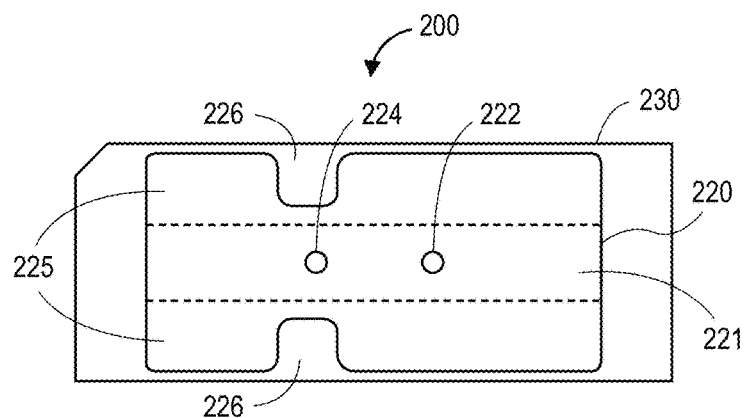
FIGS. 2A-2D illustrate top plan views of a tape assembly of the non-invasive physiological sensor of FIGS. 1A-1C, according to an embodiment of the disclosure.

FIGS. 2A-2D illustrate top plan views of the tape assembly 200 of the non-invasive physiological sensor of FIGS. 1A-1C, according to an embodiment of the disclosure. As shown, the tape assembly 200 includes the face tape 210, the trifold wrap 220, and the release liner 150. As shown in FIG. 2A, the trifold wrap 220 has a center portion 221 disposed between foldable side portions 225, which are symmetrical about the center portion 221. The center portion 221 has an emitter aperture 222 and a detector aperture 224. The emitter aperture 222 passes light from the emitter 231 (FIG. 2B) and the detector aperture 224 passes light to the detector 235 (not visible). The side portions 225 have cutouts 226 configured to accommodate the housing 140 when the side portions 225 are folded. The trifold wrap 220 has a pressure sensitive adhesive (PSA) on the component side and a Med 3044 adhesive on the center portion 221 of the patient side. The release liner 150 is removably attached to the patient side of the trifold wrap 220.

Figure 2B:
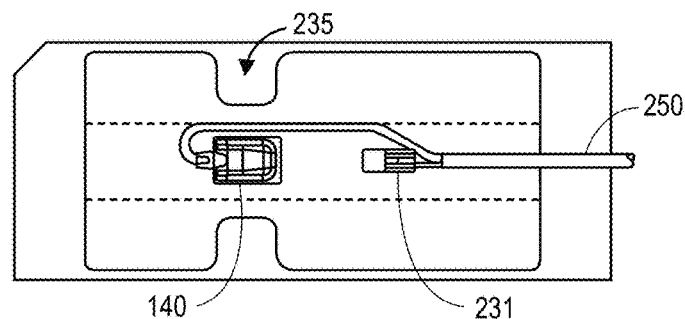
Figure 2C:
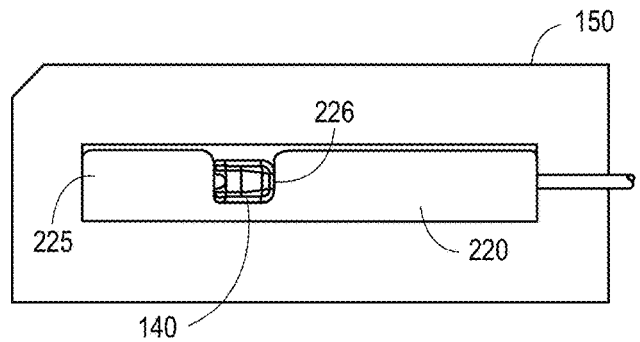
Figure 2D:
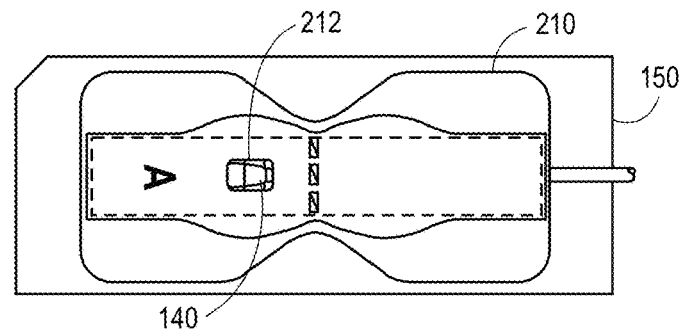

As shown in FIG. 2B, the housing assembly 250 is attached to the center portion 221 on the side opposite the release liner 150 so that the emitter 231 is aligned with the emitter aperture 222 and the detector 235 is aligned with the detector aperture 224. As shown in FIG. 2C, when assembled, the side portions 225 are folded around the housing assembly 250 so that the housing 140 protrudes through the cutouts 226. As shown in FIG. 2D, the face tape 210 is fixedly attached to the trifold wrap 220 and removably attached to the release liner 150. A face tape aperture 212 also accommodates the protruding housing 140. In one embodiment, the trifold wrap 220 is polypropylene and the face tape 210 is a laminate of Bioflex RX848P and 3M 1527ENP. As mentioned, the trifold wrap 220 and the face tape 210 include adhesives to hold the various components of the sensor 100 in place. Additionally, as mentioned above, the body 110 includes an adhesive layer that may be used to attach the sensor 100 to a tissue site of a patient.

In an embodiment, as described below, during reprocessing of the sensor 100, various components of the sensor 100 may be disassembled, tested, replaced, and/or sterilized. For example, as described below the adhesives of the trifold wrap 220 and the face tape 210 may be dissolved through application of a heated fluid, enabling efficient disassembly of the sensor. Various components may then be replaced, including the trifold wrap 220 and the face tape 210, and/or adhesives of those components. Additionally, one or more sensing components of the sensor 100, for example one or more emitters and/or detectors, may be tested and, if necessary, replaced.

Figure 3:
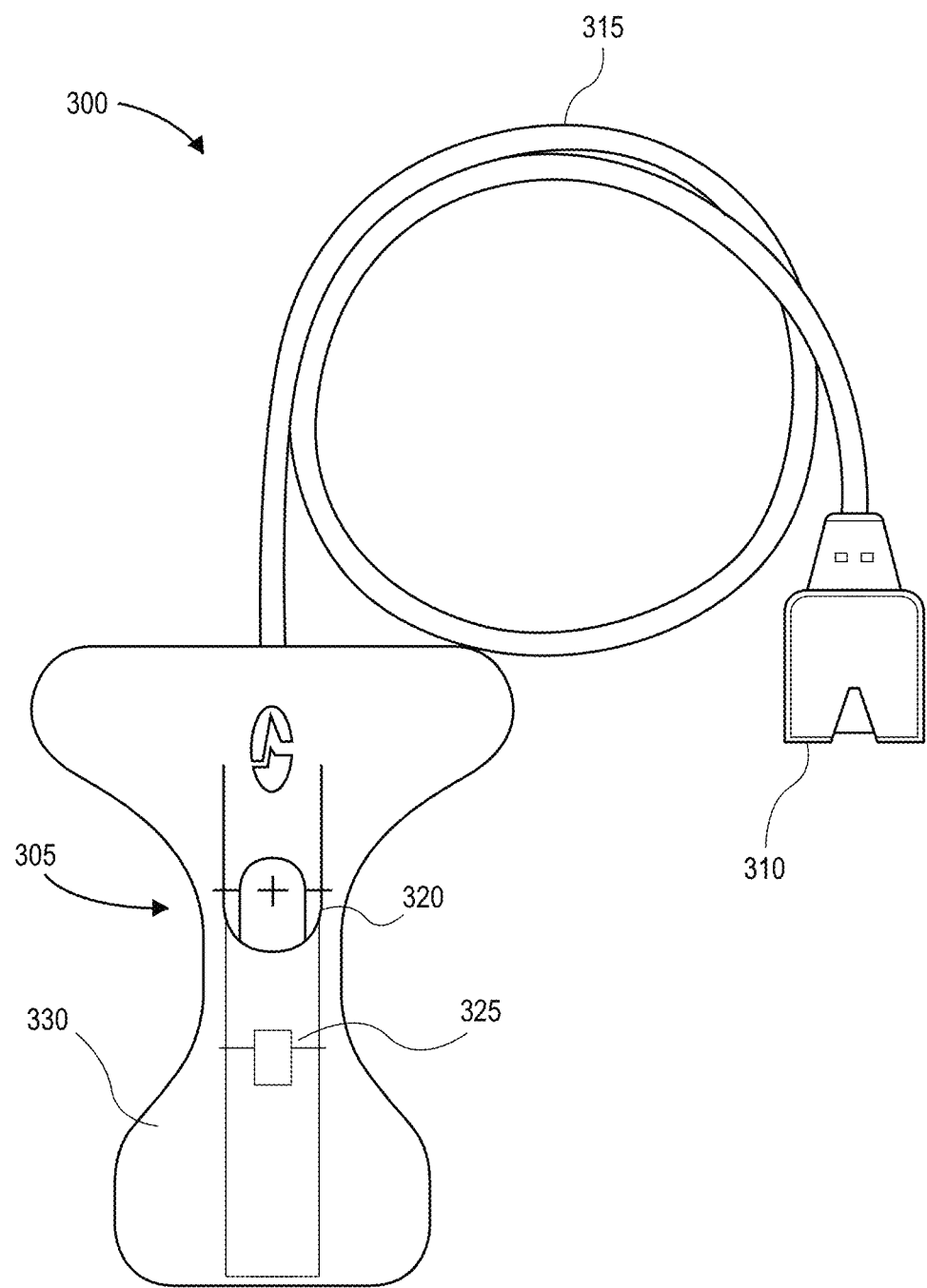
FIG. 3 illustrates another example non-invasive physiological sensor which can be used with a sensor reprocessing method, according to embodiments of the disclosure.
Figure 4A:
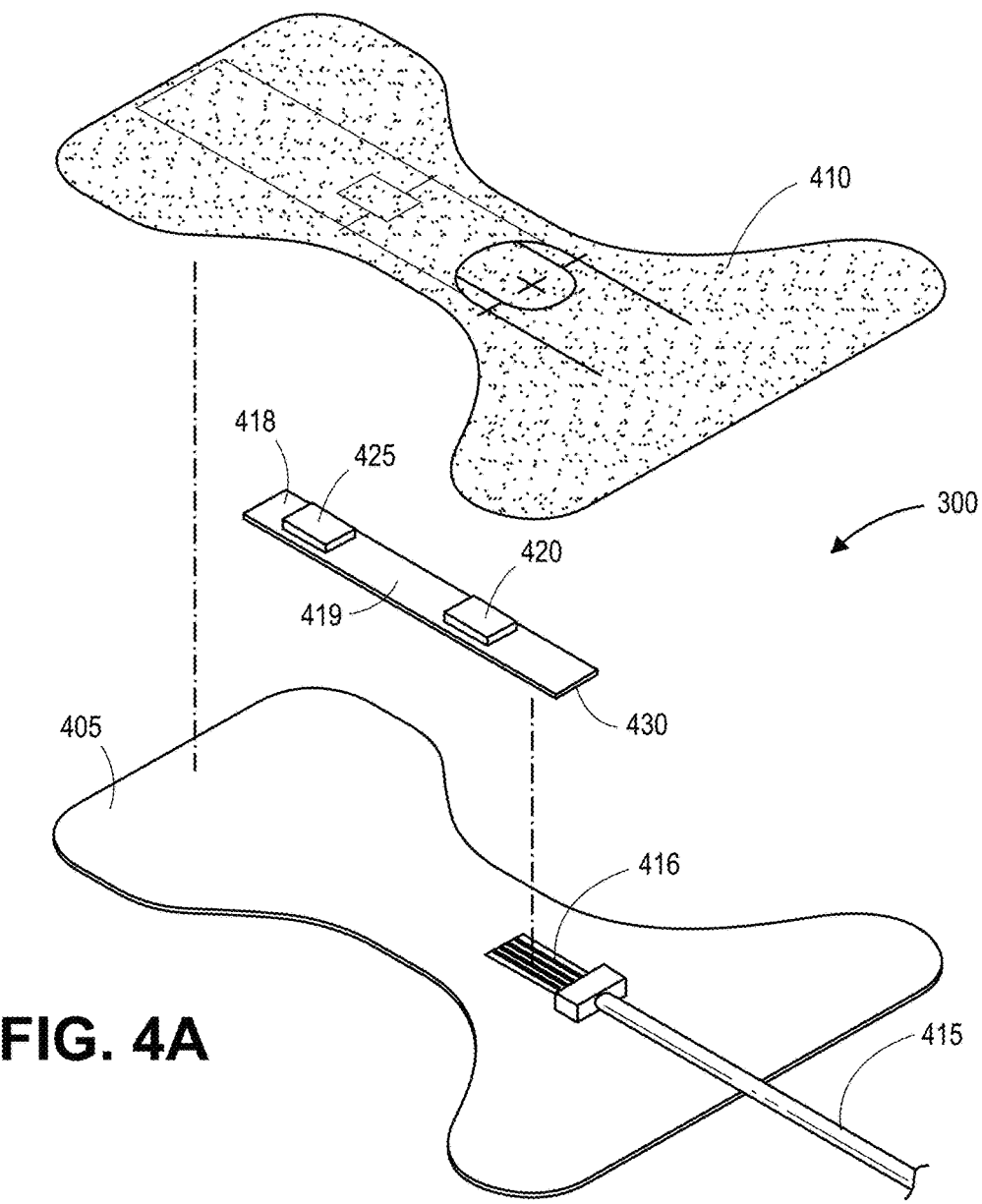
FIG. 4A illustrates an exploded perspective view of the non-invasive physiological sensor of FIG. 3, according to an embodiment of the disclosure.
Figure 4B:
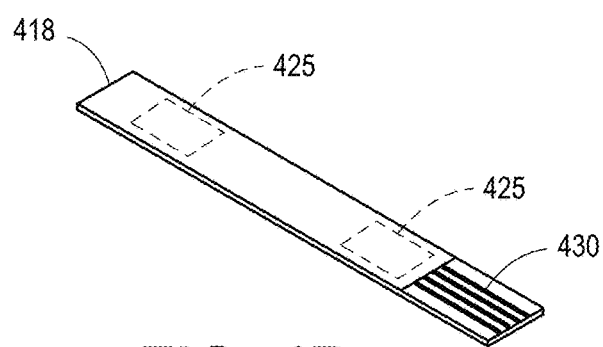
FIG. 4B illustrates a perspective view of a bottom side of a sensor portion of the non-invasive physiological sensor of FIG. 3, according to an embodiment of the disclosure.

FIGS. 3 and 4A-4B illustrate another example non-invasive physiological sensor 300 which can be used, like the sensor 100, with the sensor reprocessing methods described herein, according to various embodiments. As with the sensor 100, the sensor 300 may allow for the measurement of blood constituents and related parameters, including oxygen saturation, HbCO, HBMet and/or pulse rate. The sensor 300 may advantageously be a non-invasive optical sensor capable of emitting light and outputting one or more signals indicative of attenuation of that light by body tissue. For example, the sensor 300 may be a pulse oximeter sensor including, for example, a red emitter, an infrared emitter, and a photodiode detector. The sensor 300 may be attached to a patient's finger, earlobe, or foot. For a finger, the sensor can be configured so that the emitters project light from one side of the finger, through the outer tissue of the finger, and into the blood vessels and capillaries contained inside. The photodiode can be positioned at the opposite side of the finger to detect the emitted light as it emerges from the outer tissues of the finger. The photodiode can generate a signal based on the emitted light and relay that signal to the sensor 300. The sensor 300 can determine blood oxygen saturation by, for example, computing the differential absorption by the arterial blood of the two or more wavelengths emitted by the sensor. In certain embodiments, the sensor 300 utilizes an adhesive attachment mechanism, such as an adhesive layer, for attaching the sensor 300 to a tissue site. In some embodiments, the sensor can be disposable, re-usable, or partially re-usable and partially disposable.

The sensor 300 can include a sensor assembly 305, a patient monitor connector 310, a sensor cable 315 operatively connecting the sensor assembly 305, and a monitor connector 310. The monitor connector 310 can be adapted to connect to a patient monitor which may include a display providing readouts of measured parameters, such as oxygen saturation, pulse rate, HbCO and/or HbMet to name a few. The sensor assembly 305 can comprise one or more emitters 320 and a detector 325.

FIG. 4A illustrates an exploded perspective view of the non-invasive physiological sensor 300 of FIG. 3, according to an embodiment of the disclosure. The sensor 300 includes one or more tape layers 405 and 410, a cable assembly 415, and a sensor portion 418. The cable assembly 415 can terminate at an electric connector 416 and can be attached to one of the tape layers 405. The sensor portion 418 includes a base material 419, one or more sensing components 420 and 425 such as emitters and/or detectors, and an electrical connector 430. Sensor components can be replaced individually or together as part of the sensor portion 418. The sensor portion's electrical connector 430 can attach to the cable assembly's electrical connector 416 to form an electrical connection between the sensor portion and the cable. The sensor portion 418 can be attached to the cable assembly 415 and/or one or more tape layers 405 and 410 by various ways, such as adhesive, solder, clip holder, pressure fit and/or the like. In one embodiment, the sensor assembly 415 and sensor portion 418 are sandwiched between the first tape layer 405 and the second tape layer 410.

As the sensor portion 418 is detachable from the cable assembly 415 and/or tape layers 405 and 410, reprocessing of the sensor may be simplified. For example, the sensor portion 418 can be detached from the elongate body and replaced with a new sensor portion. By incorporating sensing components 420 and 425, such as emitters and/or detectors on the detachable modular portion, the sensing components can be easily replaced as a whole rather than individually, thus reducing reprocessing costs and reprocessing time. In one embodiment, the sensing components can be pre-tested in order to eliminate or reduce the need for testing the sensing components during the reprocessing process.

FIG. 4B illustrates a perspective view of the bottom side of the sensor portion 418 of FIG. 4A. The electrical connector 430 is shown on the bottom side of the sensor portion. However, the electrical connector can also be placed on the top side.

After the sensor 300 is used on a patient, the used sensor can be refurbished or reprocessed through a reprocessing process, as described below. Typically, refurbishing or reprocessing of medical sensors can include disassembling sensors into subcomponents, testing sensor components, replacing sensor components including disposable components, reassembly of the components, testing of the sensor and/or sterilization of the sensor. In some embodiments of the reprocessing process, the adhesive and/or adhesive layers are removed through, for example, application of a heated fluid, as described below. For example, one or more of the tape layers 405 and 410 may be removed and replaced. In an embodiment, the entire sensor assembly 305 can be replaced, reusing only the cable 315 and monitor connector 310. In certain embodiments, the cable 315 and/or monitor connector 310 can also be replaced. In some embodiments, only portions of the sensor assembly 305, such as the sensing components 320 and 325 are replaced.

In some embodiments, the whole sensor assembly 305 is replaced. Replacing the whole sensor assembly 305 can reduce or eliminate the need to disassemble the sensor and/or test components during the refurbishing process. For example, the replacement sensor can be pre-tested and/or calibrated beforehand, such as during production, so that testing the sensor components is not required. In some embodiments, the new sensor assembly includes a cable portion, typically of short length, for attachment to a reprocessed cable. In some embodiments, the cable portion can terminate in a connector for simplified attachment to the reprocessed cable.

Figure 5A:
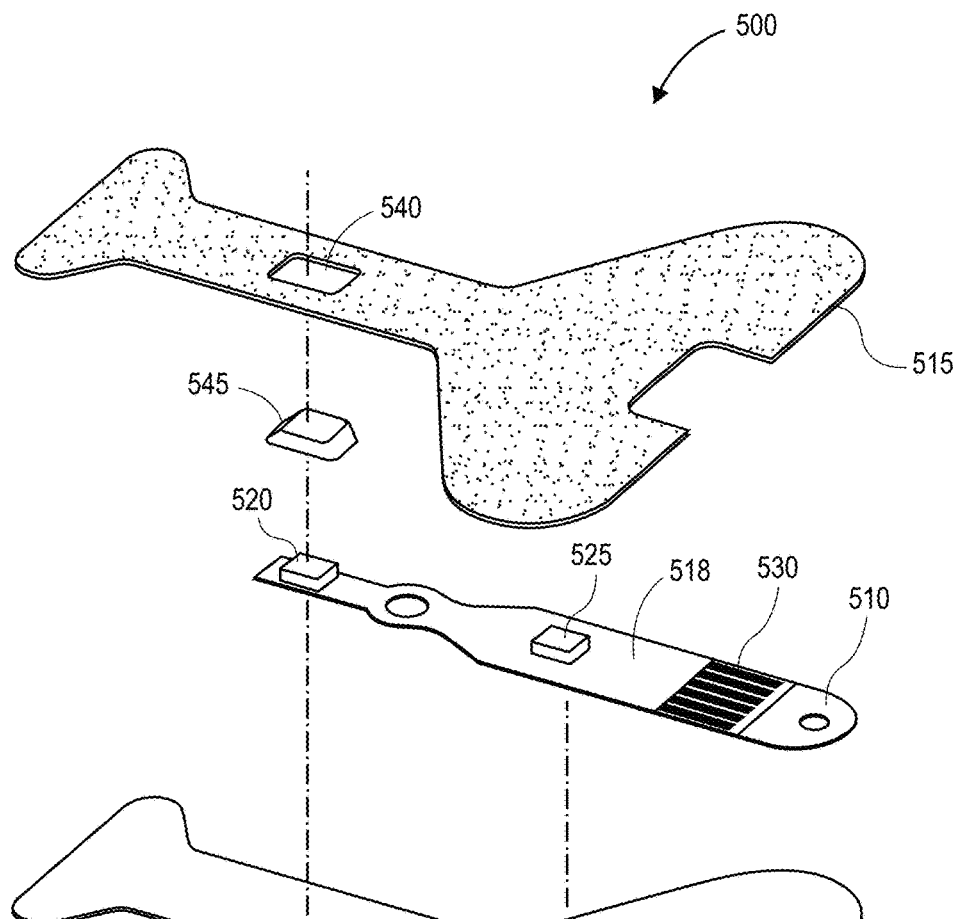
FIG. 5A illustrates an exploded perspective view of another non-invasive physiological sensor which can be used with a sensor reprocessing method, according to embodiments of the disclosure.

FIG. 5A illustrates an exploded perspective view of another non-invasive physiological sensor 500 which can be used, like the sensor 300, with the sensor reprocessing methods described herein, according to various embodiments. The sensor 500 includes one or more tape layers 505 and 515 and a sensor portion 510. The sensor portion 510 includes a base material 518, one or more sensing components 520 and 525 such as emitters and/or detectors, and an electrical connector 530. The sensor portion can further include a sensor cover 545 for one or more of the sensing components. Reusable sensor components can be replaced individually or together as part of the sensor portion 510.

In one embodiment, the base material 518, preferably a flexible material, comprises a flex circuit. The flex circuit can comprise a copper/MYLAR™ or copper/Capton™ laminant, or similar material. Alternatively, the flex circuit can be formed by depositing a conductive ink on MYLAR™, polyester, or plastic film. The flex circuit allows electrical communication between the sensing components 520 and 525 and electrical connector 530 through the conductive material on the flex circuit.

The sensing components 520 and 525 can be attached to the base material 518 through pressure sensitive adhesive (PSA), solder, clip holder, pressure fit or the like. In one embodiment, the emitter and detector are placed such that the transmission and detection field of view are through detector and emitter windows formed on the base material.

In one embodiment, the sensing components 520 and 525 are attached to the flex-circuit using pressure or thermally sensitive adhesive configured to provide a temporary bond, advantageously allowing the sensing components 520 and 525 to be detached from the sensor portion 510 by pulling the sensing components from the base material 518. As will be apparent, other attachment methods can be used that facilitate removal of sensor components in order to simplify the refurbishing process, such as nodular metal paste, mechanical attachments, or the like.

In another embodiment, the sensing components are attached to the flex-circuit using low temperature solder paste. The sensing components can be desoldered from the flex circuit. The solder can be reheated and reused or new solder can be dispensed on contacts for the detector connections and/or emitter connections in order to attach new sensing components. The solder operation is preferably performed through a direct heat reflow of the low temperature solder.

The sensor portion 510 can further comprise a flex circuit shield including an insulator film, conductive and/or nonconductive PSA. When attached to a flex circuit, a flex circuit shield can insulate the signal traces of the flex circuit from the metallization of the flex circuit shield to prevent short circuits. The sensor portion 510 can be attached to a base layer 505. In one embodiment, the base layer comprises Avery base material. Each side of the base layer can be coated with PSA adhesive.

A face stock 515 can be attached to the base layer 505 such that the sensor portion 510 is secured between the face stock and the base material. In one embodiment, the face stock 515 is advantageously constructed from a non-woven, flexible material, though woven materials can be used. Adhesive can be applied on one side of the face stock. Pressure applied to the face stock 515 bonds the face stock with the base material 505 and/or sensor portion 510. Preferably, the face stock has an aperture 540 to allow a portion of the cover 545 to protrude through the face stock. A release liner can be placed on the other side of the base material from the face stock in order to protect adhesive on that side. The release liner can be removed when the sensor is attached to a patient.

During reprocessing, the sensor assembly 500 can be disassembled into its constituent parts using methods mentioned above and described in detail below. For example, the face stock 515 can be detached from the base material 505 to expose the sensor portion 510. The sensing components 520 and 525 on the sensor portion can be replaced individually or together as part of the sensor portion 510. In one embodiment, the sensing components 520 and 525 are replaced individually with at least some of the sensor portion 510 retained. After replacing the sensing components, the sensor can be reassembled. The base layer 505, face stock 515, and/or cover 545 can be replaced or reused. New adhesive can be applied to the sensor assembly 500 and a release liner attached. Once reassembled, the sensor assembly 500 can be sterilized and then packaged for use.

Figure 5B:
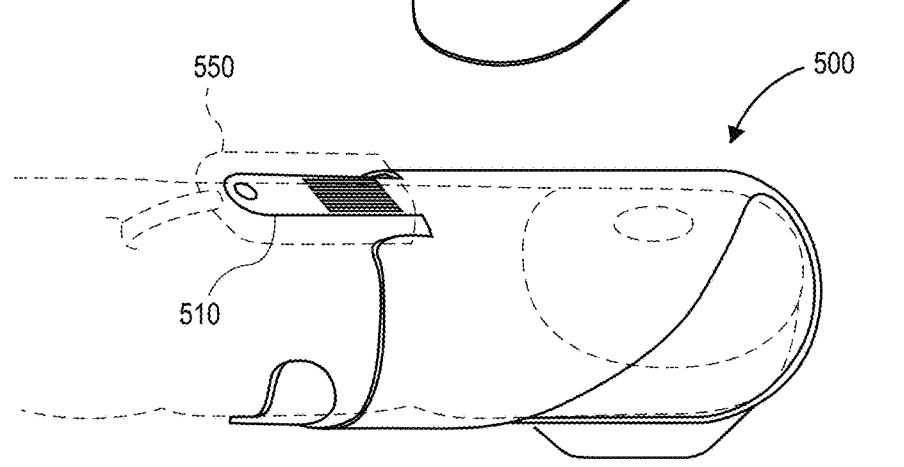
FIG. 5B illustrates the non-invasive physiological sensor of FIG. 5A attached to a tissue site, according to an embodiment of the disclosure.

FIG. 5B illustrates the disposable sensor 500 of FIG. 5A attached to a tissue site and a cable assembly. The cable assembly 550 comprises a cable and a connector attachable to the sensor assembly 500 via its sensor connector 530. The cable assembly 550 operatively connects the sensor assembly 500 to a patient monitor. The cable portion 550 can also be reprocessed with the sensor assembly 500 and replaced if defective. However, as the cable portion generally receives less wear than the sensor assembly 500, the cable portion can likely be reused without replacement of components, reducing the cost of reprocessing the sensor.

Example Sensor Reprocessing Methods

As mentioned above, example methods of reprocessing physiological sensors may include applying heat to a physiological sensor so as to efficiently remove adhesives, adhesive layers, and/or other disposable components of the sensor. Heat may be applied to the physiological sensor efficiently via a medium, such as an aqueous solution (for example, via heater water, heated oil, and/or the like). Heat can also be applied by radiation, conduction, or convection. In some embodiment, heat guns, heat lamps, heating beds, an oven or other methods of heating the sensors can be used. Reusable components of the physiological sensor may then be reassembled with new disposable components and/or adhesives to produce a reprocessed sensor. The methods may further include testing and/or replacement of various reusable sensor components, testing of the reprocessed sensor, cleaning of the reprocessed sensor and/or sensor components, and/or sterilization of the reprocessed sensor, among other steps.

Figure 6:
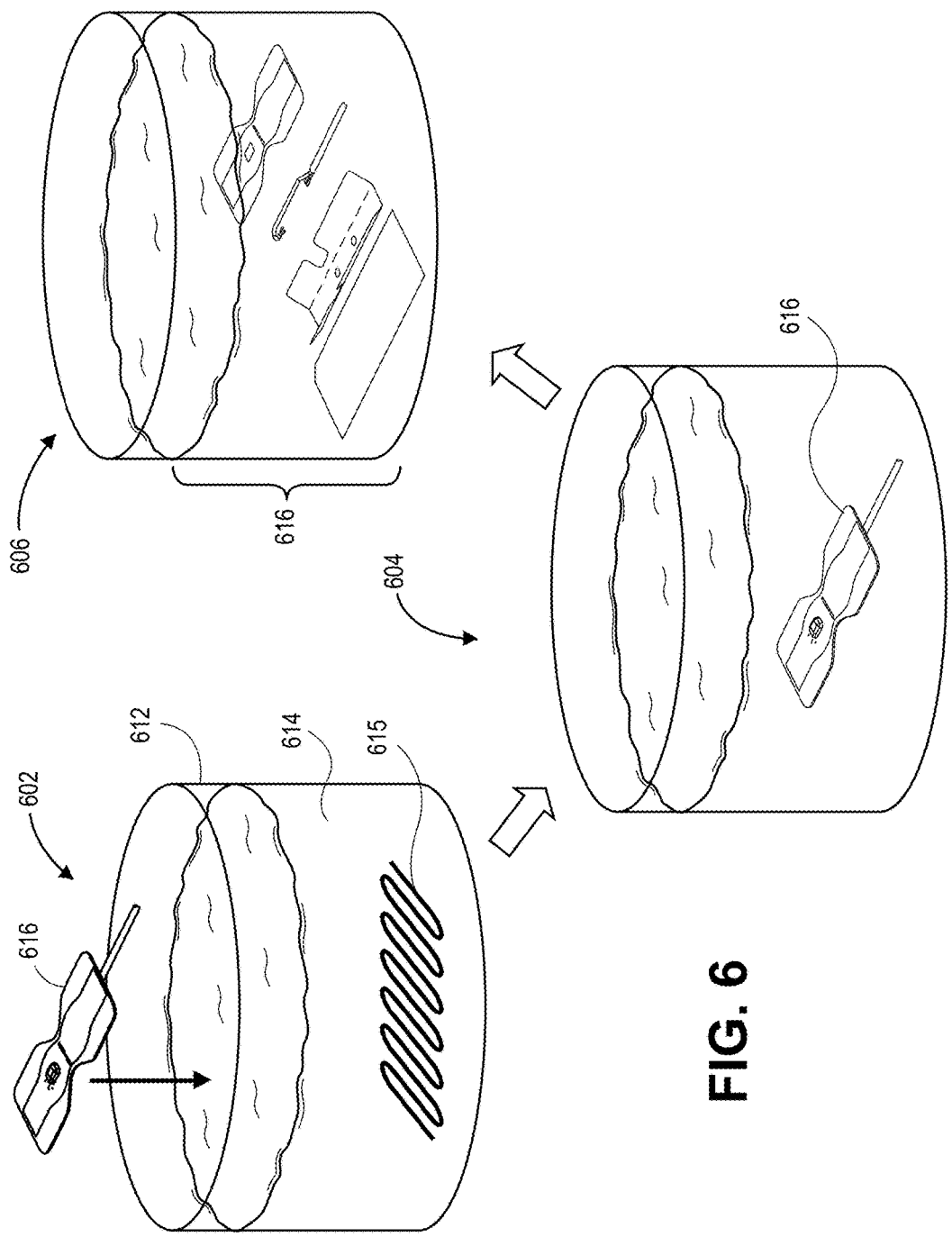
FIG. 6 illustrates a method of reprocessing a physiological sensor including bathing the physiological sensor in a heated fluid, according to an embodiment of the disclosure.
Figure 7A:
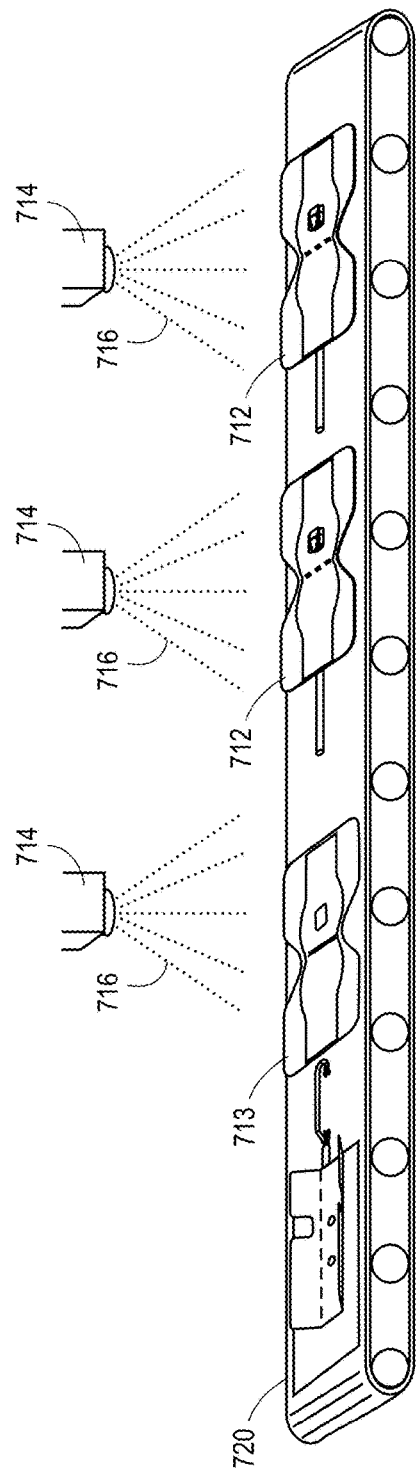
FIGS. 7A-7C illustrate additional example methods of reprocessing a physiological sensor, according to embodiments of the disclosure.
Figure 7B:
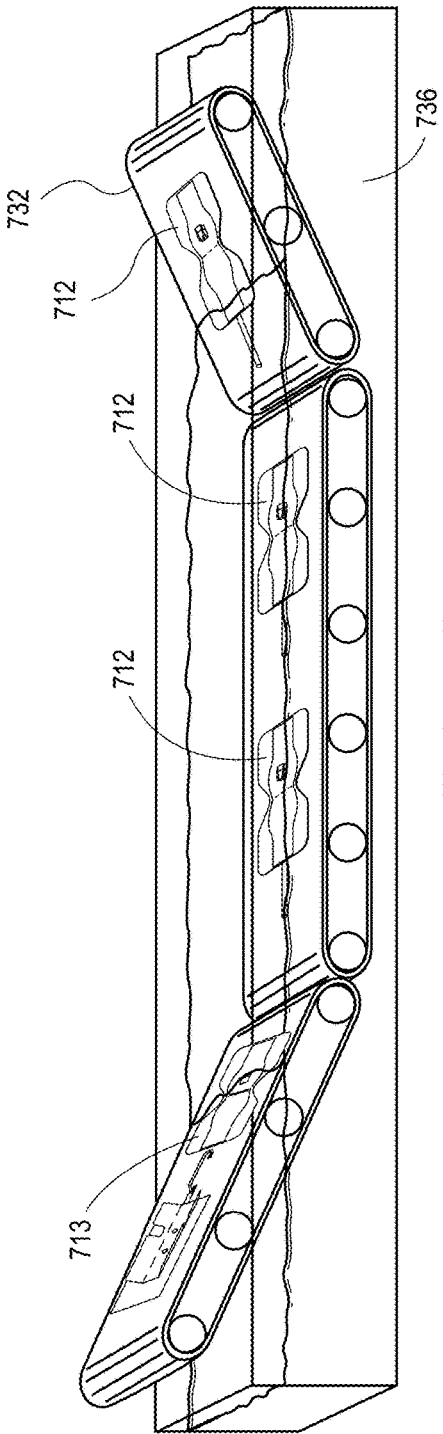
Figure 7C:
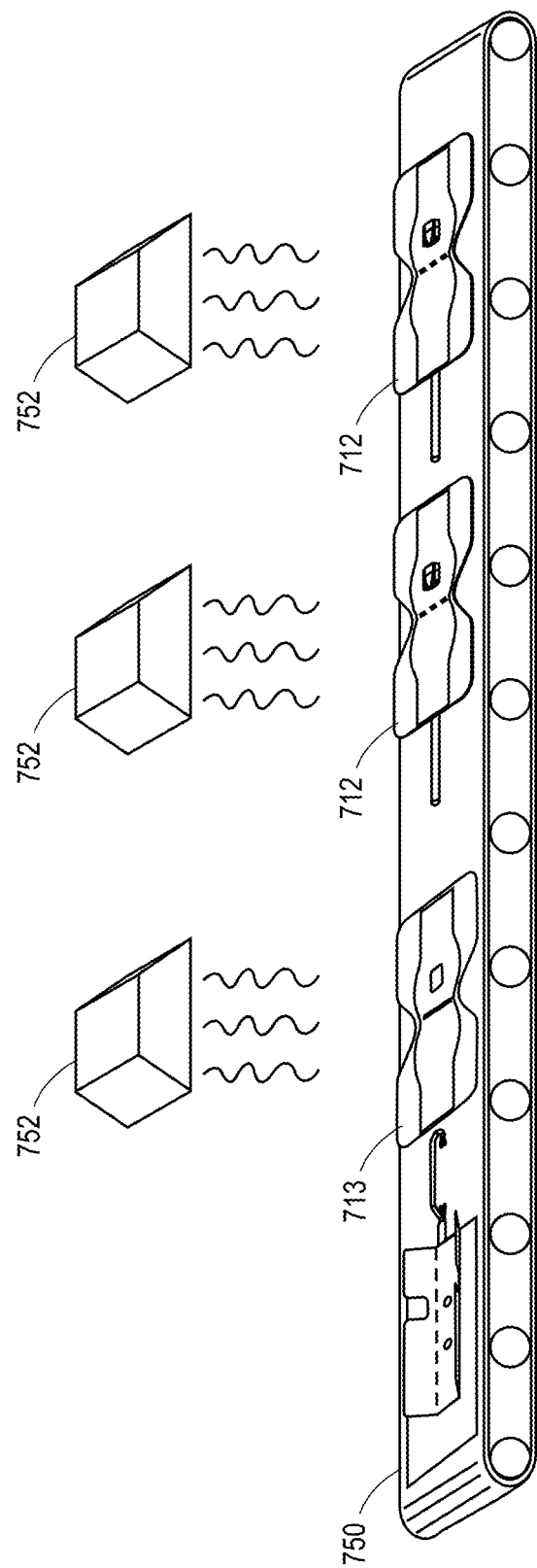

FIGS. 6 and 7A-7B illustrate example methods of applying a fluid to a sensor during processing, and are described below in reference to the methods of FIGS. 8A-8B. FIG. 7C illustrates an example method of applying heat directly to a sensor during processing, and is also described below in reference to the methods of FIGS. 8A-8B.

Figure 8A:
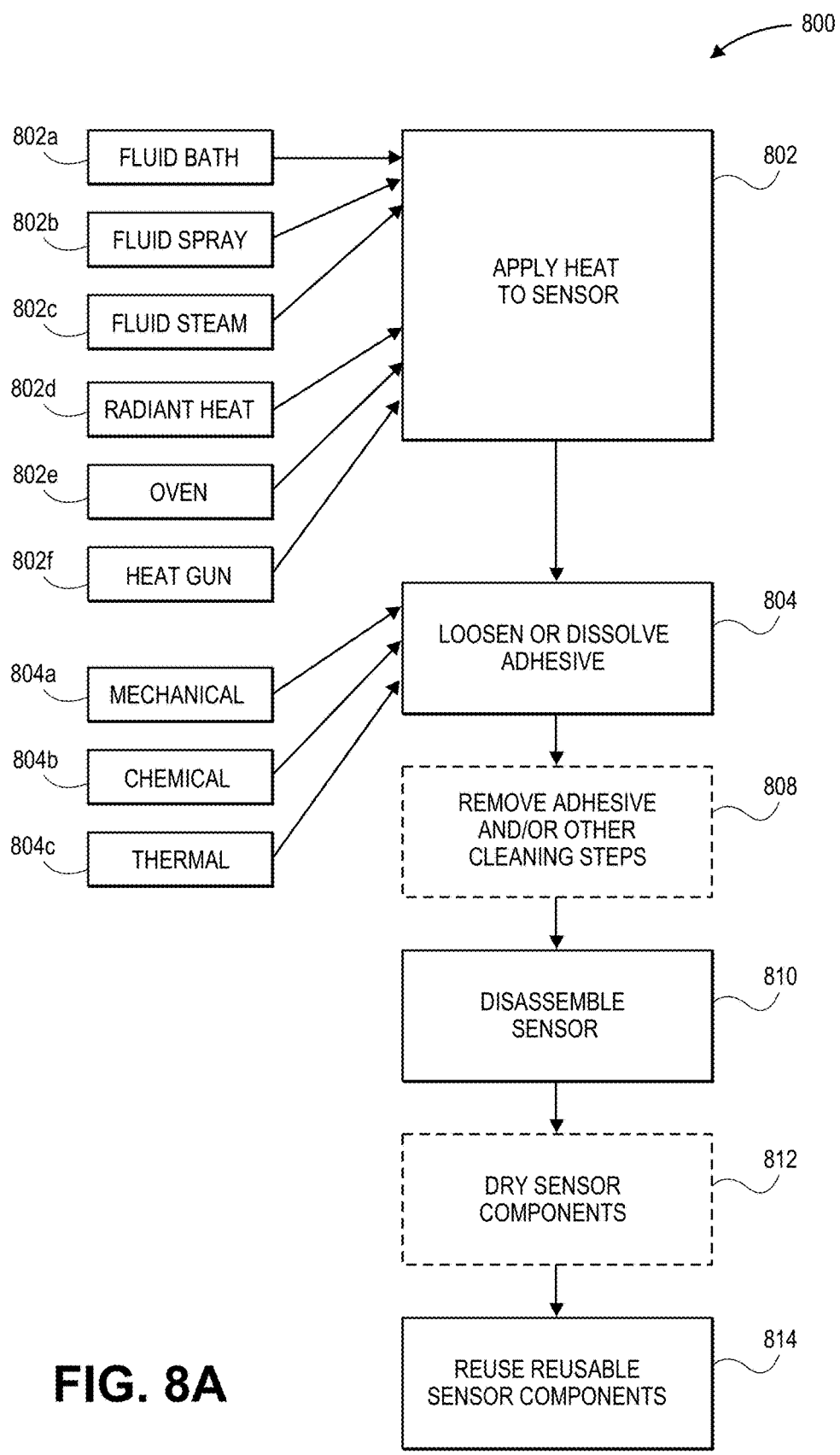
FIGS. 8A and 8B are flowcharts illustrating example methods of reprocessing a physiological sensor, according to embodiments of the disclosure.
Figure 8B:
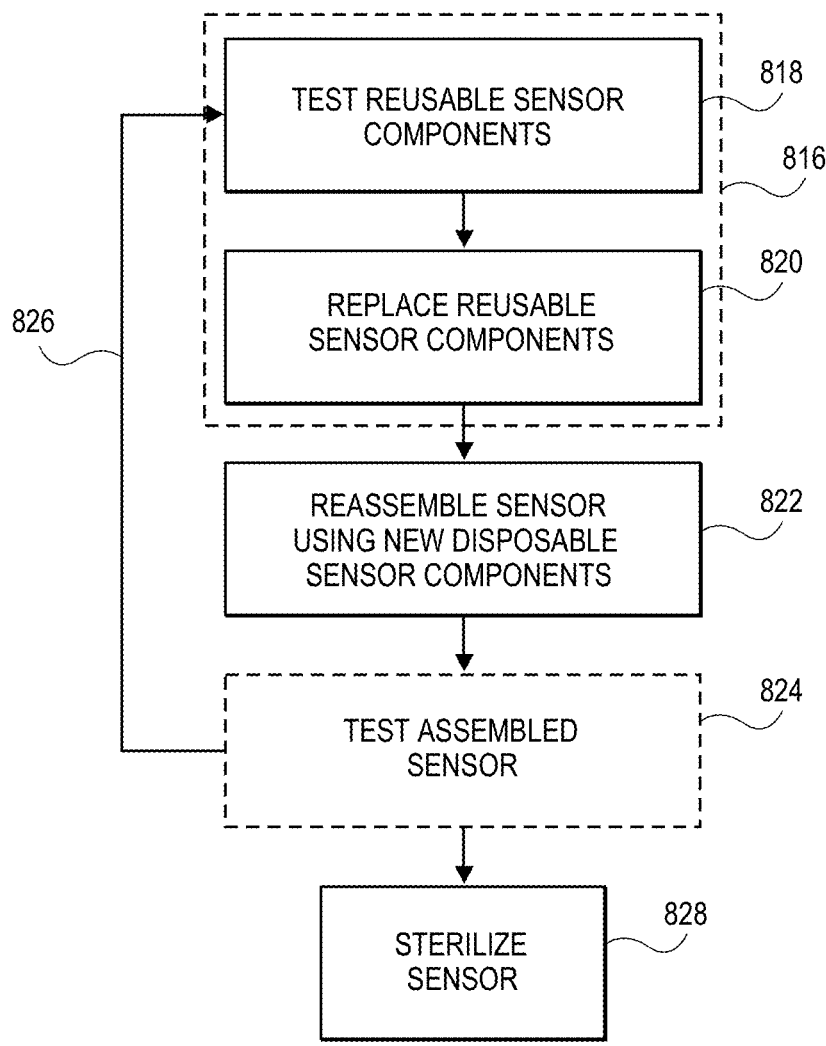

FIGS. 8A and 8B are flowcharts illustrating example methods of reprocessing a physiological sensor, according to embodiments of the disclosure. As mentioned above, the reprocessing methods of FIGS. 8A-8B may be used for any of the sensors described above in references to FIGS. 1A-1C, 2A-2D, 3, 4A-4B, and 5A-5B, as well as other types of sensors.

In some embodiments, the reprocessing methods of FIGS. 8A-8B may be performed by a computing system comprising one or more computing devices, the one or more computing devices configured to perform one or more of the logical blocks described below. The logical blocks of the reprocessing methods can be embodied as software, hardware, or a combination of software and hardware of the computing system. For example, the reprocessing methods may be embodied in software stored on non-transitory, physical computer storage such as a hard drive, optical disk, or flash memory. In some embodiments, the computing system may be part of a reprocessing system comprising one or more machines configured to disassemble sensors, replace sensor components, test sensors, and/or sterilize sensors. In one embodiment, the computing system directs or monitors the operation of the processing machines. In one embodiment, the machines operate automatically. In some embodiments, one or more logical blocks may be performed by or directed by a person. For example, the entire refurbishing process may be performed by or directed by one or more persons.

In various embodiments, the blocks of the methods of FIGS. 8A-8B may be rearranged, the methods may include more or fewer blocks, and/or the block may be combined, subdivided, and/or rearranged in order to accomplish the sensor reprocessing disclosed herein.

Referring to method 800 of FIG. 8A, blocks 802-810 show example methods of disassembling the sensor, in whole or in part, into subcomponents or individual components, including disposable and/or reusable components.

For example, at block 802 heat is applied to a sensor that is to be preprocessed. In various embodiments, as described below, the heat may be applied to the sensor via any suitable medium and/or method. Applying heat to the sensor may enable efficient disassembly of the sensor by, for example, quickly loosening and/or removing any adhesives and/or adhesive layers of the sensor. For example, one or more disposable tape layers may be removed from the sensor by the application of heat. In various embodiments, the heat applied to the sensor may melt the adhesives, soften the adhesives, weaken the adhesives, and/or cause the adhesives to release (and/or release more easily).

In various embodiments, heat may be applied to the sensor via any suitable medium and/or method. For example, heat may be applied to the sensor via a fluid that is heated in some suitable way. In an embodiment, heated fluid may be applied to the sensor as a bath, as shown by block 802a. In this embodiment, the sensor may be submersed, in whole or in part, in the heated fluid. An example of using a bath to apply the heated fluid to the sensor is shown in FIG. 6. FIG. 6 illustrates a method of reprocessing a sensor 616 in which (at 602) a bath 612 of heated fluid 614 is provided. The fluid 614 is heated by a heating element 615 in the example shown, but the fluid 614 may be heated in any other suitable manner. As shown at 604 and 606, the sensor 616 may be submersed in the bath and the heated fluid may thereby at least partially assist in disassembly of the sensor 616 into various components. Another example of using a bath to apply heated fluid to the sensor is shown in FIG. 7B. FIG. 7B illustrates a method of reprocessing multiple sensors 712 by moving the sensors along a conveyor belt 732 into a bath 736 of heated fluid. As shown in the illustration, the heated fluid may thereby at least partially assist in disassembly of the sensor into various components 713.

Returning to FIG. 8A, in some embodiments fluid may be applied to the sensor as a spray or steam, as shown at blocks 802b and 802c. FIG. 7A illustrates a method of reprocessing multiple sensors 712 by moving the sensors along a conveyor belt 720 while spraying or steaming the sensors 712 with a heated fluid 716 from one or more sprayers or steaming devices 714. As shown in the illustration, the fluid may thereby at least partially assist in disassembly of the sensor into various components 713.

In various embodiments, heated fluid may be applied to the sensor in other ways so as to enable efficient disassembly of the sensor, for example, via sprinkling and/or blasting, among others. Additionally, as described below, application of the heated fluid to the sensor may be combined with other actions (for example, mechanical processes) so as to enable even more efficient sensor disassembly.

Examples of fluids that may be applied to the sensor include, but are not limited to water or other aqueous agents and/or solutions, semi-aqueous agents (for example, an emulsion of solvents and water), hydrocarbon based solvents, halogenated solvents, oils, and/or other types of solvents and/or agents in any combination. In an embodiment, an agent/solvent to be applied to a sensor may be selected specifically for its efficacy in dissolving and/or enabling removal of adhesives and/or other contaminants from the sensor.

In another example, heat may be applied to the sensor as radiant heat (as shown at block 802d; for example, using heating elements located near the sensor), via an oven (as shown at block 802e), using a heat gun (as shown at block 802f) or heat lamp, and/or using any other suitable heat source and/or method. FIG. 7C illustrates a method of reprocessing multiple sensors 712 by moving the sensors along a conveyor belt 750 and near one or more heat sources 752 (for example, radiant heat sources and/or heat guns). As shown in the illustration, the heat sources may thereby at least partially assist in disassembly of the sensor into various components 713. In an embodiment, the conveyor belt 750 itself can be the source of the heat.

Returning to FIG. 8A, at block 804 the adhesives (and/or adhesive layers) of the sensor may be loosened, weakened, melted, softened, dissolved, and/or removed, as also described above. In an embodiment, the sensor adhesives may be loosened, weakened, melted, softened, dissolved, and/or removed efficiently simply by application of the heat, and/or the heated fluid. In other embodiments, other processes may be combined with the application of heat and/or heated fluid to enable efficient loosening, weakening, melting, softening, dissolving, and/or removal of the adhesives. For example, as mentioned above, and as shown at block 804c, thermal processes may be applied to the sensor. For example, heat may be applied, and/or the sensor may be heated before, during, and/or after application of the fluid. In an embodiment, a temperature of the heat applied to the sensor may be specific to the types of adhesives and/or adhesive layers to be removed, and/or the temperature of the heat applied may be varied as necessary and/or advantageous. In an example, an appropriate temperature and/or temperature pattern of heat to apply to the sensor may be determined according to a type of the sensor and/or one or more characteristics of the sensor (for example, a manufacturer of the sensor, a serial number of the sensor, a color of the sensor, and/or the like). In the example of a heated fluid being applied to the sensor, the heated fluid may be heated to just below a boiling point, and may be applied to the sensor as a liquid. Alternatively, the fluid may be heated such that the fluid is a steam, and may be applied to the sensor in a gas state. In other alternatives, the fluid may be heated to any other temperature, and/or may be cooled to any temperature. In an embodiment, heated water (or another aqueous solution) may be applied to the sensor. Heated water may be used so as to not damage any reusable components of the sensor, while assisting in loosening and/or removal of sensor adhesives and/or adhesive/tape layers.

In an embodiment, thermal processes may be applied to the sensor with or without the application of a fluid, and/or multiple phases of heat may be applied to the sensor at various times and/or via various mediums. For example, heat may be applied to the sensor from, for example, a heat gun at one point during reprocessing, and heat may be applied to the sensor via a fluid at another point. Heat may be applied to the sensor as the sensor moves along a conveyor belt and/or in some other manner. As mentioned above, the applied heat may cause the adhesive to be loosened, weakened, melted, softened, dissolved, and/or removed with or without the application of a fluid. In some embodiments, heat may be applied to the sensor in combination with other processes as disclosed herein.

Other examples of processes that may be combined with the application of heat to enable efficient loosening and/or removal of the adhesives include, as shown at blocks 804a and 804b, mechanical and chemical processes. For example, the sensors may be agitated or vibrated, subjected to ultrasonic waves, scrubbed, disassembled by robots, and/or subjected to solvents (as described above), among other processes. In an embodiment, a solvent may be applied to the sensor so as to dissolve adhesives, adhesive layers, and/or tape layers, while not damaging reusable components. Any combination of the above mentioned processes may be combined so as to enable efficient disassembly of the sensor. In an embodiment, multiple heated fluids may be applied to the sensor simultaneously and/or independently, and each fluid application may be combined with any process described above.

At block 808, the adhesive and/or adhesive/tape layers may be removed from the sensor. Further, other cleaning steps may be applied to the sensor. In an embodiment, the heat, fluid(s), and/or other processes applied to the sensor may simultaneously clean and/or sterilize the sensor components. At block 810, the sensor is disassembled into various sensor components, including any reusable and/or disposable sensor components as described above in reference to the sensors of FIGS. 1A-1C, 2A-2D, 3, 4A-4B, and 5A-5B. For example, the adhesive and/or adhesive/tape layers that may be removed from the sensor may include the face tape 210, the trifold wrap 220, and/or the release liner 150 of sensor 100; the tape layers 405 and/or 410 of the sensor 300; and/or the tape layers 505 and/or 515 of the sensor 500. Examples of reusable sensor components may include one or more emitters, detectors, wires, cables, connectors, housings, and/or other components of the sensor described above.

Further, in addition to the methods described above in reference to blocks 802-810, in various embodiments the sensor can be disassembled through desoldering, removing adhesive in additional steps, detaching connectors, and/or the like.

At block 812, the reusable disassembled sensor components may be dried (if, for example, a fluid was applied to the sensor), while disposable sensor components (or sensor components that are selected for disposal) may be disposed of. Drying of the sensor components may be by any suitable method including, for example, application of heat and/or low humidity environments. The sensor components may be dried in such a way that the reusable components are not damaged.

At block 814, the reusable sensor components are reused in a reprocessed sensor, as described in detail in reference to FIG. 8B.

Turning to FIG. 8B, methods of reusing reusable sensor components in a reprocessed sensor are illustrated in the flowchart. The methods may include testing and/or replacement of various reusable sensor components, testing of the assembled reprocessed sensor, cleaning of the reprocessed sensor and/or sensor components, and/or sterilization of the reprocessed sensor, among other steps.

At the blocks indicated by dashed line 816, reusable sensor components may be tested and replaced if necessary. For example, at block 818, the sensor components may optionally be tested to determine if performance of the components is within specification. Sensor components within specification can be reused. Testing of components can be skipped to reduce cost and/or speed up the refurbishing process. In an embodiment, testing can be conducted before disassembly to determine if the sensor as a whole is within specification. Generally, sensors need to meet specified sensor performance criteria determined by the manufacturer or purchaser. By testing before disassembly, out-of-specification sensing components can be detected beforehand and the sensing portion can be replaced as a whole without disassembly. In contrast, by testing after disassembly, a specific out-of-spec component can be identified, allowing reuse of the other parts of the sensing portion that are still in-spec. The timing of the testing can be chosen based on the costs of disassembly versus the savings from reusing still in-specification components. After block 818, the refurbishing process proceeds to block 820.

At block 820, sensor components may be replaced. In one embodiment, sensor components are replaced if they are determined to be out-of-spec. In another embodiment, no testing is performed and sensor components pre-determined to not meet specifications are replaced. In another embodiment, particular sensor components may be predetermined to be replaced regardless of their performance. For example, as part of the reprocessing, all or some of the sensing components can be replaced without testing. Advantageously, predetermined replacement of components can eliminate or reduce the need for testing or disassembly. After block 820, the refurbishing process proceeds to block 822.

At block 822, the sensor is reassembled. Reassembly can comprise soldering, adhesively connecting, and/or mechanically connecting various components together. Typically, the assembled sensor comprises both new components (for example, new disposable components) and at least some of the original components (for example, reusable components). After block 822, the refurbishing process proceeds to optional block 824.

At optional block 824, the assembled sensor is optionally tested to determine if the sensor works and is within specification for the particular sensor type. Testing can include testing of the assembly of the sensor components, testing of the electrical connection between sensor components, testing of sensor performance, and/or the like. If the test fails, the sensor can reenter the refurbishing process at block 818 (as indicated by arrow 826) or can be disposed of. If the sensor passes the test, the refurbishing process proceeds to block 828. In some embodiments, testing may be unnecessary during reprocessing, such as when the sensor components are pre-tested before assembling the sensor.

At block 828, the sensor is sterilized. Sterilization can occur before or after the sensor is packaged for use. The sensor can also be cleaned before sterilization. After sterilization, the sensor can be packaged for use, ending the reprocessing process.

As mentioned above, various blocks of the methods of reprocessing described in reference to FIGS. 8A-8B may be removed, divided, and/or rearranged. Further examples of method of reprocessing sensor may be found in U.S. Pat. No. 8,584,345, titled "Reprocessing of a Physiological Sensor," which is hereby incorporated by reference herein in its entirety.

Additional Embodiments

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A method for reprocessing a previously used physiological sensor, the method comprising:
   moving the sensor on a conveyor belt;
   applying, during a first phase, heat to the sensor via a first medium, wherein the first medium includes at least one of: radiant heat, a fluid bath, a fluid spray, or a fluid steam;
   after the first phase, further moving the sensor on the conveyor belt;
   applying, during a second phase occurring after the first phase, heat to the sensor via a second medium, wherein the second medium is a different medium from the first medium;
   applying to the sensor, during the first phase and/or second phase, at least one of: agitation, vibration, or ultrasonic waves;
   disassembling the sensor into sensor components including one or more reusable sensor components; and
   assembling a reprocessed sensor by attaching one or more new sensor components to at least one of the reusable sensor components.

2. The method of claim 1, wherein the first medium includes a fluid.

3. The method of claim 2, wherein the fluid comprises at least one of water, an aqueous agent or solution, a semi-aqueous agent, a hydrocarbon based solvent, a halogenated solvent, an oil, or any combination thereof.

4. The method of claim 1, wherein the heat enables disassembly of the sensor.

5. The method of claim 1, wherein the heat at least partially loosens, weakens, melts, softens, or dissolves an adhesive of the sensor.

6. The method of claim 1, wherein the heat is applied to the sensor sufficient to enable efficient removal of adhesives, adhesive layers, or tape layers.

7. The method of claim 1 further comprising:
   applying further processes to the sensor, wherein the further processes include at least one of: mechanical, chemical, or thermal.

8. The method of claim 1, wherein the second medium includes at least one of: radiant heat, a fluid bath, a fluid spray, or a fluid steam.

9. The method of claim 1 further comprising:
   removing one or more adhesive components of the sensor that are loosened by the applied heat.

10. The method of claim 9 further comprising:
    determining one or more sensor components of the sensor to be replaced,
    wherein disassembling the sensor comprises detaching the one or more sensor components to be replaced from the sensor.

11. The method of claim 10 further comprising:
    determining whether sensing performance of the reprocessed sensor meets specified sensor performance criteria; and
    sterilizing the reprocessed sensor in preparation for use.

12. The method of claim 10, wherein determining one or more sensor components comprises:
    testing performance of the one or more sensor components to determine if the performance is within specification for the sensor component.

13. The method of claim 1, wherein the one or more reusable sensor components include at least one of an emitter or a detector.

14. The method of claim 1, wherein the sensor is a pulse oximetry sensor.

15. The method of claim 1, further comprising cleaning the sensor in order to remove visible contaminants.

16. The method of claim 1, wherein the one or more reusable sensor components includes a cable.

* * * * *